US010745349B2

(12) United States Patent
Sonnenberger

(10) Patent No.: US 10,745,349 B2
(45) Date of Patent: Aug. 18, 2020

(54) CERAMIDE DIMER, METHOD FOR THE PRODUCTION THEREOF, AND USE OF SAME

(71) Applicant: PATENTPORTFOLIO 2 S.À.R.L., Luxembourg (LU)

(72) Inventor: Stefan Sonnenberger, Sandersdorf-Brehna (DE)

(73) Assignee: PATENTPORTFOLIO 2 S.À.R.L., Luxembourg (LU)

( * ) Notice: Subject to any disclaimer, the term of this patent is extended or adjusted under 35 U.S.C. 154(b) by 0 days.

(21) Appl. No.: 15/748,058

(22) PCT Filed: Jul. 26, 2016

(86) PCT No.: PCT/EP2016/067818
§ 371 (c)(1),
(2) Date: Mar. 15, 2018

(87) PCT Pub. No.: WO2017/017104
PCT Pub. Date: Feb. 2, 2017

(65) Prior Publication Data
US 2018/0237387 A1 Aug. 23, 2018

(30) Foreign Application Priority Data

Jul. 28, 2015 (DE) .................. 10 2015 214 295

(51) Int. Cl.
| | | |
|---|---|---|
| *A61K 8/46* | (2006.01) | |
| *A61Q 19/00* | (2006.01) | |
| *C07C 319/14* | (2006.01) | |
| *C07C 323/60* | (2006.01) | |

(52) U.S. Cl.
CPC .............. *C07C 323/60* (2013.01); *A61K 8/46* (2013.01); *A61Q 19/00* (2013.01); *C07C 319/14* (2013.01)

(58) Field of Classification Search
CPC ....... C07C 323/60; C07C 319/14; A61K 8/46; A61Q 19/00
See application file for complete search history.

(56) References Cited

U.S. PATENT DOCUMENTS

| | | | | |
|---|---|---|---|---|
| 5,863,886 | A * | 1/1999 | Tracy | ..................... C11D 1/525 510/470 |
| 9,018,405 | B2 | 4/2015 | Wolf | |
| 2012/0129933 | A1 | 5/2012 | Wolf | |

FOREIGN PATENT DOCUMENTS

| | | | |
|---|---|---|---|
| EP | 2 266 950 A1 | 12/2010 | |
| EP | 2266950 A1 * | 12/2010 | ........... C07C 235/08 |

OTHER PUBLICATIONS

Neubert et al. Skin Pharmacol. Physiol. 2016, 29, 130-134. (Year: 2016).*
Bittman et al., "Anticancer activity of a ceramide analog containing a disulfide linkage," *Cancer Letters* 251(1): 53-58 (2007).
Ohlsson et al., "ω-Mercapto analogs of naturally occurring lipids," *Tetrahedron Letters* 40(10): 2011-2014 (1999).
Sahle et al., Skin Diseases Associated with the Depletion of Stratum Corneum Lipids and Stratum Corneum Lipid Substitution Therapy, *Skin Pharmacology and Physiology* 28: 42-55 (2015).
European Patent Office, International Search Report in International Application No. PCT/EP2016/067818 (dated Oct. 20, 2016).
European Patent Office, Written Opinion in International Application No. PCT/EP2016/067818 (dated Oct. 20, 2016).
International Bureau of WIPO, International Preliminary Report on Patentability in International Application No. PCT/EP2016/067818 (dated Oct. 20, 2016).

* cited by examiner

*Primary Examiner* — Amanda L. Aguirre
(74) *Attorney, Agent, or Firm* — Leydig, Voit & Mayer, Ltd.

(57) ABSTRACT

The invention relates to ceramide dimers in which the amino alcohols are linked together by amide bonds via a dicarboxylic acid. The dicarboxylic acids have at least one sulfur atom in the chain. The invention also relates to a method for producing the ceramide dimers. The ceramide dimers are used as active ingredients to stabilize the skin barrier in cosmetic and pharmaceutical preparations.

16 Claims, 2 Drawing Sheets

CERAMIDE DIMER, METHOD FOR THE PRODUCTION THEREOF, AND USE OF SAME

CROSS-REFERENCE TO RELATED APPLICATIONS

This patent application is the U.S. national phase of International Application No. PCT/EP2016/067818, filed on Jul. 26, 2016, which claims the benefit of German Patent Application No. 10 2015 214 295.7, filed Jul. 28, 2015, the disclosures of which are incorporated herein by reference in their entireties for all purposes.

The invention relates to ceramide dimers of two ceramides, in which the amino alcohols are linked with amide bonds via a dicarboxylic acid. The dicarboxylic acids have at least one sulfur atom in the chain. The invention also relates to a method for synthesis of ceramide dimers. Ceramide dimers are used as active ingredients to stabilize the skin barrier in cosmetics and pharmaceutical preparations.

The barrier function of human skin is controlled by the higher-level structure of the lipids of the stratum corneum (SC). SC lipids form lipid double layers and consist of the free fatty acids, cholesterol and its derivatives as well as the ceramides, where the ceramides play a key role. A deficiency of ceramides in the human stratum corneum is responsible for various skin diseases (Sahle, F. F., Gebre-Mariam, T., Dobner, B., Wohlrab, J., Neubert, R. H. H., Skin Diseases Associated with the Depletion of Stratum Corneum Lipids and Stratum Corneum Lipid Substitution Therapy, Skin Pharmacology and Physiology (2015); 28:42-55). To eliminate ceramide deficiencies in the SC in the past, ceramides were supplied externally through topical preparations, but these ceramides are subject to a not insignificant metabolism.

In the patent literature, ceramide dimers have been described for stabilization of the skin barrier, their hydrophilic head groups such as the amino alcohols sphingosine and phytosphingosine being linked together by a long-chain dicarboxylic acid. This long-chain dicarboxylic acid consists of either a chain of $CH_2$ groups or a chain of $CH_2$ groups interrupted by a defined number of ether groups (EP 2 266 950 A1).

Against this background, the object of the present invention was to make available compounds for stabilizing the skin barrier, wherein it should be possible to synthesize these compounds in a particularly simple manner.

This object is achieved by the features of the ceramide dimer and the method for producing the ceramide dimer described herein. Compounds according to the invention and the advantageous refinements thereof are also described.

According to the invention, a ceramide dimer of two ceramides is made available, formed by means of a dicarboxylic acid having a carbon chain with 4 to 40 carbon atoms (optionally 10 to 40 carbon atoms, preferably 20 to 30 carbon atoms), each being formed by means of an amide bond with two amino alcohols functioning as hydrophilic head groups, wherein the carbon chain of the dicarboxylic acid is substituted by at least one sulfur atom (optionally 1-5 sulfur atoms, preferably 1 to 3 sulfur atoms, in particular 1 to 2 sulfur atoms).

The dicarboxylic acid is preferably an α,ω-dicarboxylic acid, i.e., the dicarboxylic acid has one carboxyl group each at the beginning and at the end of its carbon chain.

The invention thus also relates to bipolar ceramide dimers in which the amino alcohols sphingosine and phytosphingosine are connected to one another by a long-chain dicarboxylic acid. The amino alcohols sphingosine and phytosphingosine can be substituted by other terminal polar groups. The polarity and thus the bipolar character of the compounds are increased by the additional hydrophilic groups, which results in a greater water binding capacity.

The dicarboxylic acid consists of $CH_2$ groups interrupted by a defined number of thioether groups in the chain. The bipolar character of these ceramides is made possible by the dicarboxylic acid which has a chain length of 4 to 40 carbon atoms (optionally 10 to 40 carbon atoms, preferably 20 to 30 carbon atoms). Due to the membrane-spanning property of these compounds, the stability of the stratum corneum lipid double layers and thus the barrier function of the stratum corneum are increased.

The dicarboxylic acid according to the invention with at least one thioether group may preferably be constructed from at least two building blocks by one or more alkylation steps.

At least one of the amino alcohols (preferably both) preferably consists of a sphingosine molecule wherein the sphingosine molecule and/or the ceramide especially preferably has a sphingosine, phytosphingosine, sphinganine or 6-hydroxysphingosine base body according to one of the general formulas I through IV:

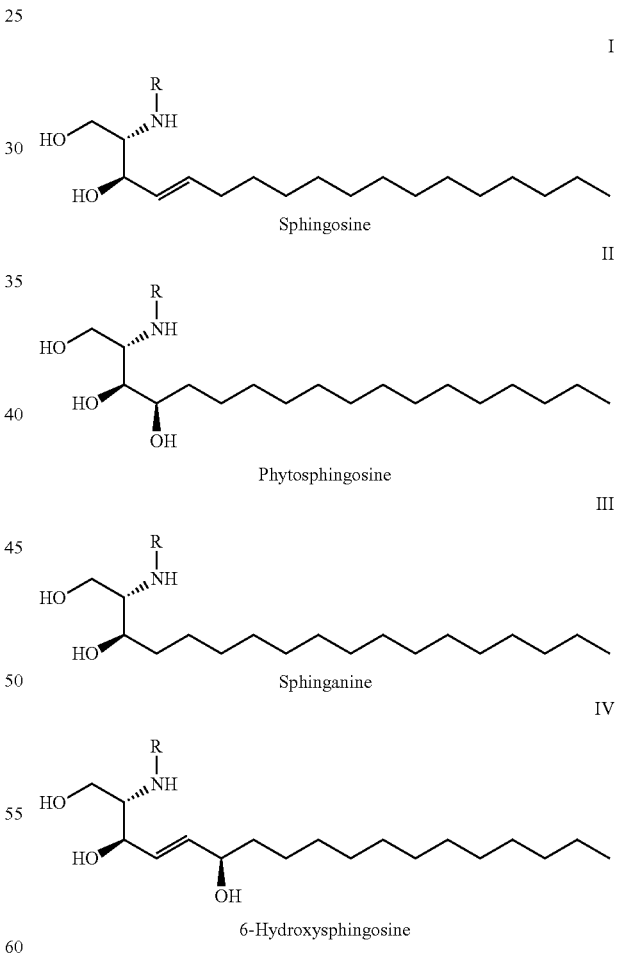

where R=linear or branched dicarboxylic acid radical with 4 to 40 carbon atoms (optionally 10 to 40 carbon atoms, preferably 20 to 30 carbon atoms), wherein the carbon chain of the dicarboxylic acid radical is substituted by at least one sulfur atom, i.e., the dicarboxylic acid radical contains at least one thioether group.

In addition, it is preferable for the dicarboxylic acid to be substituted with one or more sulfur atoms in the chain according to one of the general formulas V or VI:

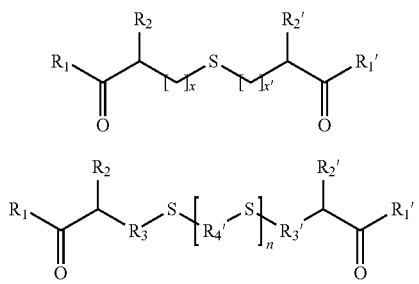

where
R$_1$=sphingoid base body according to any one of formulas I to IV;
R$_1$'=sphingoid base body according to any one of formulas I to IV;
R$_2$=H or OH;
R$_2$'=H or OH,
R$_3$=linear or branched C$_1$-C$_{18}$ alkyl radical;
R$_3$'=linear or branched C$_1$-C$_{18}$ alkyl radical;
R$_4$'=linear or branched C$_2$-C$_{20}$ alkyl radical;
x=1-18;
x'=1-18; and
n=at least 1.

It is preferable for the head group of the ceramide dimer to have at least one additional hydrophilic group. This at least one additional hydrophilic group is preferably selected from the group consisting of
- Amino acids, in particular serine, threonine, lysine, arginine, histidine, asparagine, aspartic acid, glutamine, glutamic acid, tyrosine and tryptophan,
- Polyols, in particular ethanediol, propanediol or glycerol,
- Sugar, in particular glucose or galactose,
- Amino sugars or amino sugar derivatives with dissociable carboxyl group, in particular glucuronic acid or galacturonic acid,
- Organic acids, in particular succinic acid, malic acid or citric acid,
- Inorganic acids, in particular phosphoric acid or sulfuric acid,
- Choline, ethanolamine, monomethyl ethanolamine, dimethyl ethanolamine and
- Combinations thereof.

Preferably the at least one additional hydrophilic group is bound either by the hydroxyl group or the hydroxymethylene group of the sphingoid base body.

The ceramide dimers can be supplied for use as pharmaceutical drugs. This refers in particular to the treatment of skin diseases, preferably diseases in which there is a disturbance in the composition of the stratum corneum lipids of the skin, especially preferably diseases in which there is a disturbance in the composition of the stratum corneum lipids of the skin with regard to their ceramide content, α-hydroxyceramide content and/or sphingosine content.

The ceramide dimers according to the invention may preferably be used to produce a cosmetic preparation, in particular a colloidal preparation, preferably as a cream, ointment, lotion, suspension, gel, spray, cosmetic oil, nanoparticle, nanocapsule, microemulsion or liposomes.

According to the invention, a method for producing a ceramide dimer according to the invention is also made available, comprising the coupling of a first carboxylic acid group and a second carboxylic acid group of a dicarboxylic acid whose carbon chain is substituted by at least one sulfur atom, with the amino group of one sphingoid base body each, thus forming two amide bonds. The amide bonds thus join the a and w positions of the carboxylic acid in a chemically covalent bond to the position of the amino group of the sphingoid base body.

In a preferred specific embodiment, the dicarboxylic acid before coupling is produced by a method comprising the following steps:
a) Reacting at least one α,ω-diol with 2 to 20 carbon atoms or an α,ω-dihalide with 2 to 20 carbon atoms, preferably with thiourea, to form an α,ω-dithiol, in particular octane-1, 8-dithiol;
b) Reacting the α,ω-dithiol with a base, preferably potassium hydroxide and/or potassium tert-butanolate to form the alkali salt of the α,ω-dithiol, in particular to form dipotassium octane-1,8-dithiolate; and
c) Reacting the alkali salt of the α,ω-dithiol with two ω-functionalized carboxylic acids each with 2 to 20 carbon atoms, preferably with the addition of a condensation means and an auxiliary base or an activator, in particular to form 12,21-dithiadotriacontanedioic acid.

Furthermore, the dicarboxylic acid can be provided before coupling by a method comprising the following steps:
a) Reacting at least one ω-halo-α-carboxylic acid with 2 to 20 carbon atoms, preferably with thiourea to form an ω-mercapto-α-carboxylic acid, in particular 11-mercapto-1undecanoic acid;
b) Reacting the ω-mercapto-α-carboxylic acid with a base, preferably potassium hydroxide and/or potassium tert-butanolate, to form the alkali salt of the ω-mercapto-α-carboxylic acid, in particular to form dipotassium undecane-11-thiolate-1-carboxylate; and
c) Reacting the alkali salt of the ω-mercapto-α-carboxylic acid with an α,ω-dihalide with 2 to 20 carbon atoms, preferably with the addition of a condensation agent and an auxiliary base or an activator, in particular to 12,21-dithiadotriacontanedioic acid.

Furthermore, the dicarboxylic acid before coupling can be provided by a method comprising the following steps:
a) Reacting at least one ω-halo-α-carboxylic acid with 2 to 20 carbon atoms, preferably with thiourea to yield an ω-mercapto-α-carboxylic acid, in particular 11-mercapto-1undecanoic acid;
b) Reacting the ω-mercapto-α-carboxylic acid with a base, preferably potassium hydroxide and/or potassium tert-butanolate to form the alkali salt of ω-mercapto-α-carboxylic acid, in particular dipotassium undecane-11-thiolate-1-carboxylate, and
c) Reacting the alkali salt of the ω-mercapto-α-carboxylic acid with an ω-halocarboxylic acid with 2 to 20 carbon atoms, preferably with the addition of a condensation agent and an auxiliary base or an activator, in particular to 16-thiahentriacontanedioic acid.

In the reaction in step a) above, the following steps are preferably carried out:
i) Reacting thiourea to yield a thiouronium salt, preferably in 95 vol % ethanol with heating for 5 to 20 hours;
ii) Reacting the thiouronium salt with an alkali hydroxide to yield an alkali thiolate, preferably in 5N sodium hydroxide solution with heating for 1 to 5 hours; and iii) Reacting the alkali thiolate with acid to form a thiol, preferably in 2N hydrochloric acid.

In the reaction in step b), a reaction with potassium tert-butanolate may take place in >99.5 vol % ethanol at 0° C.

The reaction in step c) preferably takes place with heating for 5 to 20 hours.

The coupling in the process according to the invention preferably takes place with the addition of a coupling reagent, especially preferably in combination with an auxiliary base and/or an activator, wherein in particular N,N'-bis[(3S,4R)-1,3,4-trihydroxyoctadec-(2S)-2-yl]-12,21-dithiadotriacontanediamide is formed.

In a preferred embodiment, the carboxylic acid is an α,ω-dicarboxylic acid, preferably an α,ω-dicarboxylic acid with
  a) 4 to 40 carbon atoms, preferably 10 to 40 carbon atoms, especially preferably 20 to 35 carbon atoms, in particular 25 to 30 carbon atoms, and/or
  b) 1 to 5 sulfur atoms, preferably 1 to 3 sulfur atoms, in particular 1 to 2 sulfur atoms.

The ceramide dimers according to the invention are preferably synthesizable by the method according to the invention.

On the basis of the following figures and the example, the subject matter according to the invention will be explained in greater detail without attempting to restrict them to the specific embodiments presented here.

Figure 1:
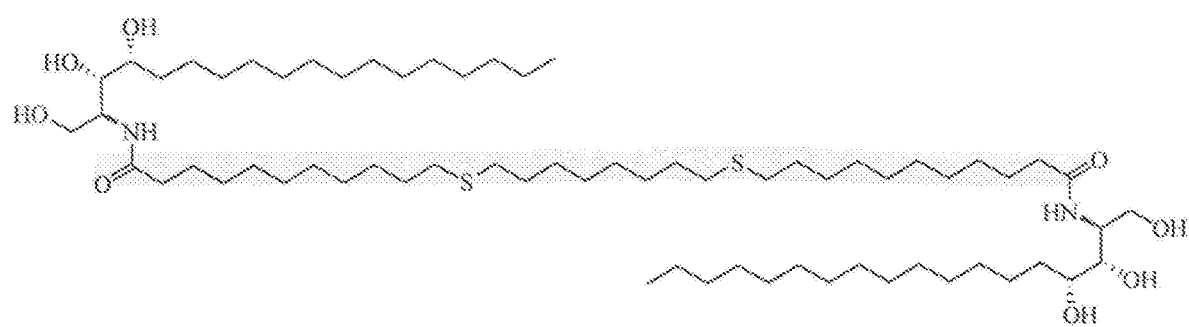
FIG. 1 shows a first compound according to the invention having two thioether groups.

The reactants for the compound shown in FIG. 1 are 1,ω-diols and 1,ω-dibromides of different chain lengths that are converted to 1,ω-dithiols. The dithiols in the form of their sodium and potassium salts are then reacted with ω-functionalized carboxylic acid derivatives. In the specific case of the structure illustrated in FIG. 1, the commercially available 11-bromoundecanoic acid is used.

The dicarboxylic acid given as an example here can also be obtained from the dipotassium salt of 11-mercaptoundecanic acid as well as 1,8-dibromooctane and/or form the bis-tosylate and bis-mesylate of octane-1,8-diol.

Figure 2:
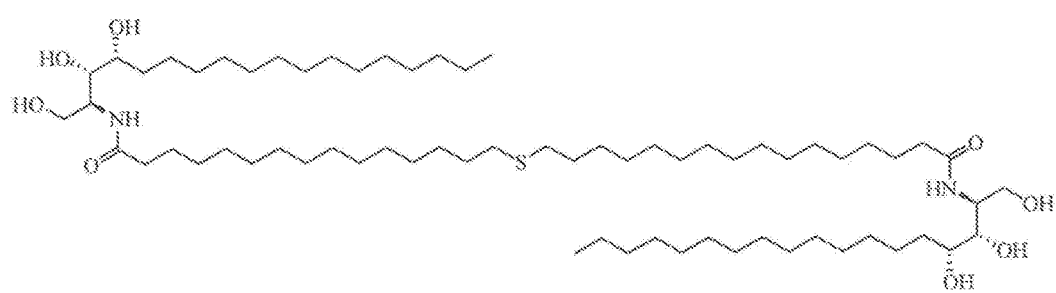
FIG. 2 shows a second compound according to the invention having one thioether group.

The compound shown in FIG. 2 is obtained from 15-bromo- and 15-hydroxypentadecanoic acid and potassium sulfide.

The binding of the dicarboxylic acids according to the invention to the sphingosine and phytosphingosine base body and/or their derivatives takes place by using PyBOP as the condensation agent and an auxiliary base. A second method includes the use of EEDQ as an activating reagent.

EXAMPLE 27.20 g (0.1 mol) 1,8-dibromooctane and 16.73 g (0.22 mol) thiourea are heated at reflux for 10 hours in 10 mL 95% ethanol. The precipitate formed on cooling is filtered with suction and washed with a small amount of ethanol. For saponification, the dithiouronium salt is added to 120 mL 5N sodium hydroxide solution and heated at reflux for 2 hours. Next the reaction mixture is acidified with 2N hydrochloric acid, and the aqueous phase is separated from the dithiol phase. The dithiol is dried over sodium sulfate and then filtered out. The filter residue is washed several times with diethyl ether, and the ether phases are combined with the dithiol phase, concentrated and dried over phosphorus pentoxide.

This yields 13.20 g raw product of octane-1,8-dithiol. Before being used further, the corresponding amount is purified by column chromatography.

Reaction of the α,ω-dithiol with an alkali hydroxide, forming the alkali salt of α,ω-dithiol, i.e., for dipotassium octane-1,8-dithiolate.

To synthesize the dithiolate solution, 2.25 g (20 mmol) potassium tert-butanolate is suspended in 60 mL absolute ethanol, cooled to 0° C., and then a solution consisting of 1.78 g (10 mmol) octane-1,8-dithiol in 20 mL absolute ethanol is added slowly by drops. Next the mixture is stirred further for 2 hours while cooling with ice.

1.20 g (30.0 mmol) sodium hydroxide is added to a solution of 7.96 g (30.0 mmol) 11-bromoundecanoic acid in 60 mL absolute methanol. The batch is stirred for 2 hours, then the methanol is removed in a rotary evaporator and the residue is dried over phosphorus pentoxide for 2 hours. The resulting solid are suspended in 60 mL absolute ethanol and heated to 50° C. A freshly prepared dipotassium octane-1,8-dithiolate solution is added slowly by drops to the suspension, and then the reaction batch is heated at reflux for 10 hours.

For workup, 8.65 g (131.0 mmol) potassium hydroxide is added, and then the mixture is heated for 1 hour at reflux. The precipitate formed on cooling is filtered out with suction through a frit, then washed three times with 20 mL ethanol and once with 20 mL distilled water. The resulting solids from the frit are added to 100 mL of a 2M sulfuric acid, stirred for 30 minutes and then extracted four times with 100 mL chloroform each time. The combined chloroform phases are washed with 100 mL 2M sulfuric acid and then concentrated. The residue is recrystallized from heptane.

The invention claimed is:

1. A ceramide dimer formed by amide binding with two amino alcohols, each having one amino group functioning as the hydrophilic head group, by a dicarboxylic acid with a carbon chain having 4 to 40 carbon atoms, wherein the carbon chain of the dicarboxylic acid radical is substituted by at least one sulfur atom, and optionally with one or more hydroxyl groups, wherein each of the two amino alcohols, independently, is composed of a $C_{18}$ alkyl chain or a $C_{18}$ alkenyl chain with one carbon-carbon double bond, and each of the amino alcohols has the one amino group functioning as the hydrophilic head group and two or three hydroxyl groups.

2. The ceramide dimer according to claim 1, wherein at least one of the amino alcohols contains a sphingosine molecule, wherein the sphingosine molecule has a sphingoid base body according to any one of the general formulas I through IV:

I sphingosine:

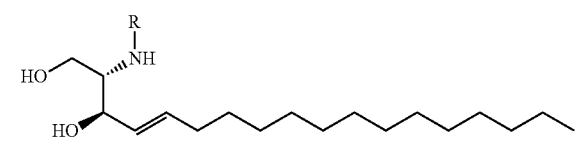

phytosphingosine:

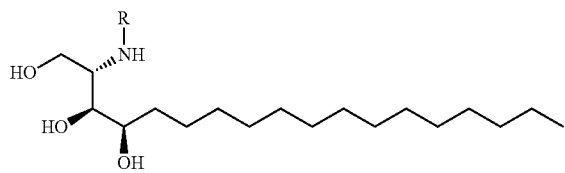

II sphinganine:

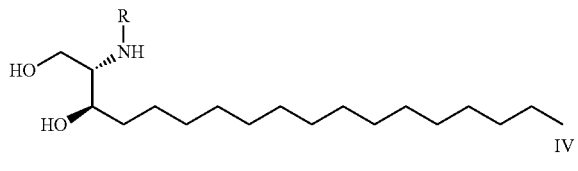

III

6-Hydroxysphingosine:

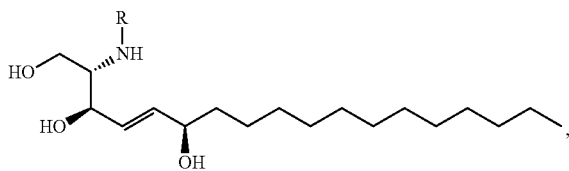

IV wherein R=linear or branched dicarboxylic acid radical with 10 to 40 carbon atoms, wherein the carbon chain of the dicarboxylic acid radical is substituted by at least one sulfur atom.

3. The ceramide dimer according to claim 2, wherein the dicarboxylic acid radical is substituted with one or more sulfur atoms in the chain according to general formula V or VI:

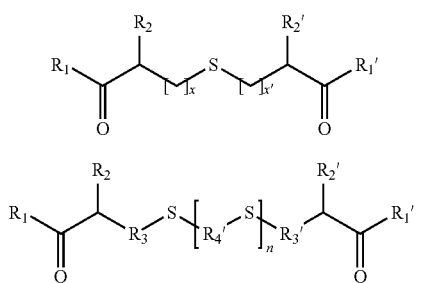

where
$R_1$=sphingoid base body according to any one of formulas I to IV;
$R_1'$=sphingoid base body according to one of formulas I to IV;
$R_2$=H or OH;
$R_2'$=H or OH,
$R_3$=linear or branched $C_1$-$C_{18}$ alkyl radical;
$R_3'$=linear or branched $C_1$-$C_{18}$ alkyl radical;
$R_4'$=linear or branched $C_2$-$C_{20}$ alkyl radical;
x=1-18;
x'=1-18; and
n=at least 1.

4. A pharmaceutical composition comprising a ceramide dimer according to claim 1 and a pharmaceutically acceptable carrier.

5. A cosmetic preparation comprising a ceramide dimer according to claim 1 and a cosmetic carrier.

6. A method of treating a skin disease comprising administering a ceramide dimer according to claim 1.

7. The method of claim 6, wherein the skin disease arises from a disturbance in the composition of the stratum corneum lipids of the skin.

8. A method for producing a ceramide dimer according to claim 1, comprising coupling a first and a second carboxylic acid group of the dicarboxylic acid, with the amino group of a each of the two amino alcohols, whereby two amide bonds are formed.

9. The method for producing a ceramide dimer according to claim 8, further comprising preparing the dicarboxylic acid by a method comprising:
a) reacting at least one α,ω-diol with 2 to 20 carbon atoms, or an α,ω-dihalide with 2 to 20 carbon atoms, with thiourea, to form an α,ω-dithiol;
b) reacting the α,ω-dithiol with a base, thereby forming an alkali salt of the α,ω-dithiol; and
c) reacting the alkali salt of the α,ω-dithiol with two ω-functionalized carboxylic acids, wherein the functionalization is a leaving group.

10. The method for producing a ceramide dimer according to claim 8, further comprising preparing the dicarboxylic acid by a method comprising:
a) reacting at least one w-halo-a-carboxylic acid having a carbon chain with 2 to 20 carbon atoms with thiourea to form an ω-mercapto-α-carboxylic acid;
b) reacting the ω-mercapto-α-carboxylic acid with a base, thereby forming the alkali salt of the ω-mercapto-α-carboxylic acid; and
c) reacting the alkali salt of the ω-mercapto-α-carboxylic acid with an α,ω-dihalide.

11. The method for producing a ceramide dimer according to claim 8, further comprising preparing the dicarboxylic acid by a method comprising:
a) reacting at least one ω-halo-α-carboxylic acid having a carbon chain with 2 to 20 carbon atoms with thiourea to form an ω-mercapto-α-carboxylic acid;
b) reacting the ω-mercapto-α-carboxylic acid with potassium hydroxide and/or potassium tert-butanolate, thereby forming the alkali salt of ω-mercapto-α-carboxylic acid; and
c) reacting the alkali salt of the ω-mercapto-α-carboxylic acid with an ω-halocarboxylic acid with 2 to 20 carbon atoms.

12. The method for producing a ceramide dimer according to claim 11, wherein the following steps are carried out in the reaction in step a):
i) reacting a thiourea with the at least one ω-halo-α-carboxylic acid to form a thiouronium salt;
ii) reacting the thiouronium salt with an alkali hydroxide to yield an alkali thiolate with heating for 1 to 5 hours; and
iii) reacting the alkali thiolate with acid to form the ω-mercapto-α-carboxylic acid.

13. The method for producing a ceramide dimer according to claim 11, wherein in the reaction in step b), the reaction with potassium tert-butanolate is conducted at 0° C. in >99.5 vol% ethanol.

14. The method for producing a ceramide dimer according to claim 11, wherein the reaction in step c) is conducted by heating for 5 to 20 hours.

15. The method for producing a ceramide dimer according to claim 8, wherein the coupling is carried out with the addition of a coupling reagent, an auxiliary base and/or an activator.

16. The method for producing a ceramide dimer according to claim 8, wherein the carboxylic acid is an α,ω-dicarboxylic acid with
  a) 10 to 40 carbon atoms and
  b) 1 to 5 sulfur atoms.

* * * * *